United States Patent [19]

Chance

[11] Patent Number: 4,669,129
[45] Date of Patent: Jun. 2, 1987

[54] EARMUFF APPARATUS FOR USE WITH HEADSETS

[76] Inventor: Richard L. Chance, P.O. Box 1044, Woodland Park, Colo. 80863

[21] Appl. No.: 848,589

[22] Filed: Apr. 7, 1986

[51] Int. Cl.[4] ............................................. A41D 21/00
[52] U.S. Cl. ........................................ 2/209; 181/129; 381/187
[58] Field of Search ........... 2/209; 179/156 R, 182 R, 179/156 A, 182 A, 184

[56] References Cited

U.S. PATENT DOCUMENTS

| 2,989,598 | 6/1961 | Touger et al. | 179/182 R |
| 4,071,717 | 1/1978 | Fidi et al. | 179/182 R |
| 4,546,215 | 10/1985 | Ferraro | 179/182 R X |

FOREIGN PATENT DOCUMENTS

| 0639189 | 11/1936 | Fed. Rep. of Germany | 179/182 R |
| 0588176 | 1/1925 | France | 179/182 R |
| 2538204 | 6/1984 | France | 179/182 R |

Primary Examiner—Peter Nerbun
Attorney, Agent, or Firm—Timothy J. Martin

[57] ABSTRACT

An earmuff assembly releaseably attached to a headset commonly used with radio and audio playback units in order to protect the user's ears in inclement weather. The assembly includes a muff body formed by a thermal covering, surrounding a core element, and the muff body has a soft front face positionable against the ear. The muff body has a central opening to telescopically receive an earphone to orient the earphone at a location adjacent the ear. The muff body is secured to the headset, for example, by a cover plate defined by a disc covered with fabric that extends over the opening, with the muff body and the cover plate connected together by a mating hook and loop fastening strip. Alternatively, attachment may be by means of an elastic panel. The core element may, if desired, be stiffened by an annular plate.

15 Claims, 4 Drawing Figures

EARMUFF APPARATUS FOR USE WITH HEADSETS

BACKGROUND OF THE INVENTION

The present invention generally relates to ear protection, and is specifically directed to earmuffs adapted for use with headsets. Accordingly, the present invention is useful as an auxillary device which may be releaseably secured to a headset to protect the wearer's ears against exposure to the elements.

In recent years, there has been a dramatic increase in the popularity of portable radio and audio playback units. Many owners of such equipment, such as stereo cassette playing apparatus, not only enjoy operating their playback units in protected surroundings, such as their homes, but also these individuals have found pleasure from use of their playback units in an outdoor environment. Examples of individuals who often use the units in the outdoors include joggers, skiers, fishermen and the like many of whom desire year-around enjoyment of their playback units. Since these playback units provide audible signals through lightweight headsets having relatively small earphones adapted to be positioned over the ear opening, the major portions of the ear remain exposed during use, which can cause discomfort and even risk of frostbite during cold weather. The use of caps, hats and earmuffs is often difficult and uncomfortable when such headsets are used, since these headsets includes a headband which encircles the upper portion of the head to support the earphones.

The problem of ear protection for the cold weather user of a headset has been recognized in the past. U.S. Pat. No. 4,546,215 issued Oct. 8, 1985 to Ferraro discloses a detachable earmuff for a headset in order to protect the user of a headset in cold weather. In this patent, a thin thermal covering receives, along its perimeter, a spring-like framework which supports the covering in a cup shaped configuration that fits over the user's ear. The spring framework and thermal covering has a partible entrance separation so that it may be clipped around the headband of a headset adjacent the earphone so that the headband enters the earmuff at the apex of its cup shaped configuration.

While the earmuff shown in the Ferraro patent provides basic protection against inclement weather, there remains a need for an earmuff having even greater thermal protection properties which earmuff may readily be attached to a headset. There is a further need for such a thermal protector, in the form of an earmuff, that may be used with a headset without significantly interfering with the sound reproduction provided by the earphone.

SUMMARY OF THE INVENTION

It is an object of the present invention to provide a novel and useful earmuff that is attachable to a headset so as to permit operation of the while protecting the user's ears from cold conditions.

It is another object of the present invention to provide an earmuff that is quickly and easily secureable around the earphone of a headset and supported by the headband thereof so as to protect the user's ears in cold weather.

It is a further object of the present invention to provide an earmuff which may be used as an auxillary attachment to an audio headset assembly used in connection with a playback unit where such earmuff protects the user's ears without significantly interfering with the sound reproduction of the audio signals presented through the headset.

It is yet another object of the present invention to provide a protective earmuff which may be used comfortably in conjunction with the headset of an audio playback unit which earmuff is exceptionally comfortable to wear and easy to attach and remove from the headset for outdoor and indoor use, respectively.

The broad form of the present invention is therefore directed to an earmuff assembly that is releaseable secureable to a headset to protect a person's ears while the headset is worn in inclement weather. The earmuff according to the broad form of the preferred embodiment of the present invention includes a core element that has a soft, comfortable front surface that is covered by a thermal protective covering to define a muff body. The core element is provided with an opening adapted and sized to receive the earphone of a headset and may be constructed as a pair of annular members which are secured to one another on opposite sides of a relatively stiff, plastic annular plate that prevents excessive lateral deflection of the core element. Securing means are provided to releaseably secure the muff body to the headset while the earphone is positioned within the muff body so that the soft front surface of the core element and thermal protective covering may be positioned over the person's ear. In one form of the invention, the securing means is defined by a cover plate that is secured to the rear surface of the muff body by mated hook and loop fastening elements; in another form of the invention, the securing means is formed by an elastic pocket-like structure sewn onto the muff body.

These and other objects of the present invention will become more readily appreciated and understood from a consideration of the following detailed description of the preferred embodiment when taken together with the accompanying drawings, in which:

DETAILED DESCRIPTION OF THE PREFERRED EMBODIMENT

The present invention is directed to a thermal earmuff for use on headsets such as those commonly used with portable playback units, such as cassette recorders or radios. Accordingly, the present invention provides an earmuff assembly that is releaseably secureable to the headset so that the ears of the wearer may be protected from inclement weather while still being able to listen to music, information and the like provided by the playback unit.

Figure 1:
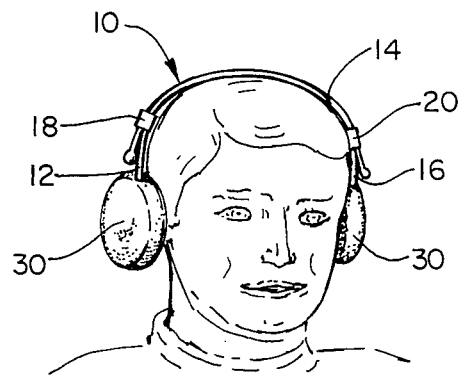
FIG. 1 is a perspective view of the thermal earmuff according to the preferred embodiment of the present invention shown attached to a headset and worn on a person's head.
Figure 2:
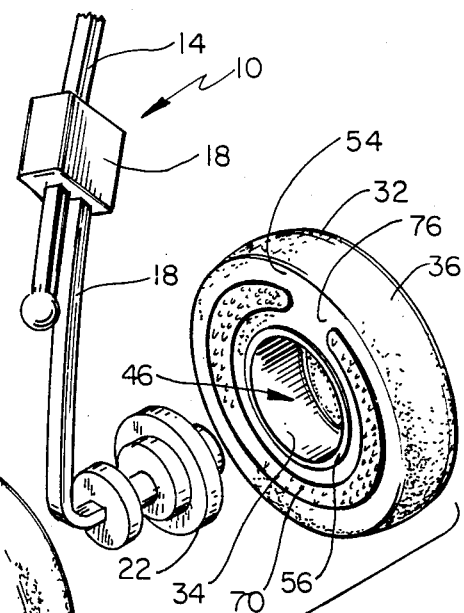
FIG. 2 is an exploded view in perspective showing the muff body and cover member according to the preferred embodiment of the present invention used with an earphone of a headset.
Figure 3:
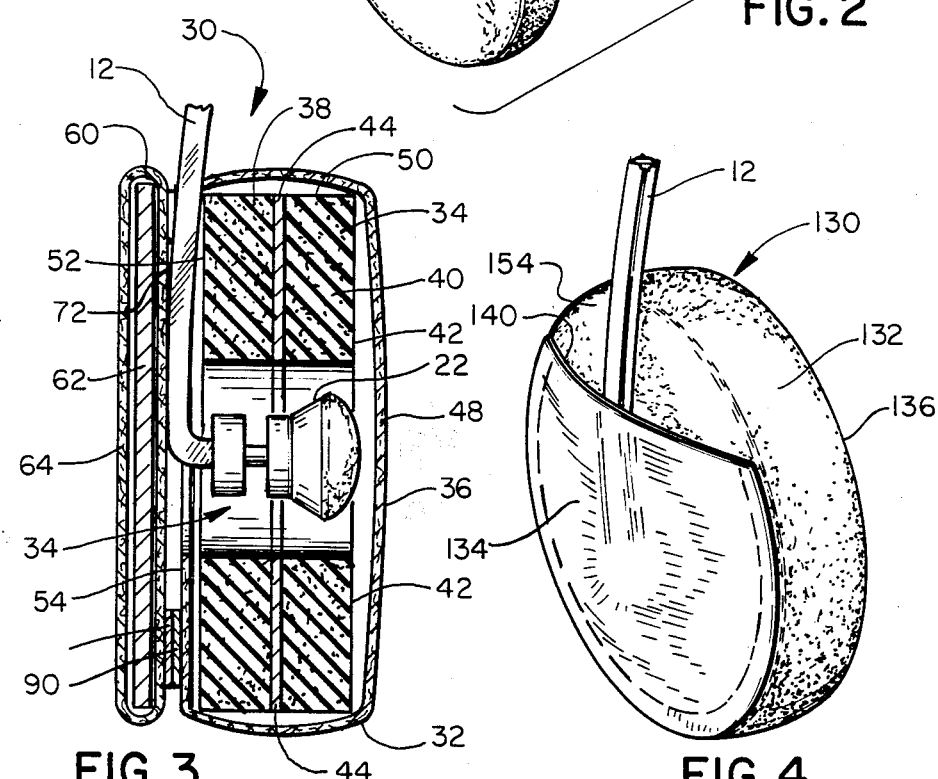
FIG. 3 is a cross-sectional view of the thermal earmuff shown in FIG. 2 secured about an earphone and headband.

As is shown in FIGS. 1, 2 and 3, a typical playback unit has a headset 10 that is formed by headband pieces 12, 14 and 16. Headband pieces 12 and 16 support connectors 18 and 20 which slideably receive opposite ends of headband piece 14. As is shown in FIG. 2, headband 10 supports an earphone, such as earphone 22, all of which is known in the art. The present invention is directed to an earmuff assembly 30 which receives earphone 22 so as to permit the wearer to hear the recorded information or radio broadcast. Earmuff assembly 30 may be comfortably worn with a headset to protect the wearer's ears against inclement weather, as is shown in FIG. 1, with the structure of earmuff assembly 30 is best shown in FIGS. 2 and 3.

In these figures, muff assembly 30 includes a muff body 32 and a cover member 60. Muff body 32 is formed by a core element 34 and a thermal covering 36 that extends around core element 34. Core element 34 includes a pair of annular core members 38 and 40 which are formed out of a relatively soft material such as foam rubber, so that core element 34 has a relatively soft front surface 42 that may be positioned adjacent the ear of the wearer. Core members 38 and 40 are secured by means of any suitable adhesive on opposite sides of an annular plate 44 to form a torus. Plate 44 is constructed of a relatively stiff plastic material to prevent excessive lateral deflection of the core element. Core members 38 and 40 have similarly sized central openings so that a composite opening 46 extending completely through core element 34 in the preferred form of the present invention. It should be appreciated, however, that opening 46 need not extend all the way through core element 34, but that it should be of sufficient depth to receive and position earphone 22 adjacent front surface 42.

Covering 36 is formed of any suitable thermal material, such as a thermal cloth, with covering 36 including a front portion 48 that extends across front surface 42 of core element 34, around side surface 50 and overlaps onto back surface 52 of core element 34. While core element 34 may be mounted in core element 36 in any suitable manner known in the art, preferably, covering 36 includes an elastic back portion 54 that overlaps onto back surface 52 to define a cover opening 56 formed coextensively with entryway 47 of opening 46.

A back cover member 60 defines a securing means to secure earphone 22 in telescopic engagement with opening 46. As is shown in FIG. 3, cover 60 is defined by a stiff disc-like plastic plate 62 that is enclosed by a covering 64, which may be selected to be a similar fabric covering to covering 36. In order to secure cover member 60 onto muff body 32, mateable hook and loop fastening strips are provided on the facing surfaces thereof. As is shown in FIG. 3, filiform strip 70 is secured in any suitable manner, such as by sewing, adhesive or the like, onto elastic portion 54 of covering 36 and mated loop strip 72 is similarly secured to covering 64 surrounding plate 62. Filiform strip 70, as is shown in FIG. 2, is preferrably configured in a C-shape so that it has a small gap 76 between its ends. Gap 76 is sized to permit projection of headband element 12 laterally outwardly of the earmuff assembly when cover 60 is secured to muff body 30 as is shown in FIG. 3. Accordingly, it should be appreciated that the configuration of loop strip 70 has an annular configuration with strips 70 and 72 having a common diameter. Due to the compressability of core element 50, annular strip 72 does not need to have a gap corresponding to gap 76, with the omission of this gap removing any problem of rotational orientation of cover member 60 on muff body 32.

From the foregoing, it should be appreciated that the user of muff assembly 30 first removes cover 60 from the muff body and inserts earphone 22 through cover opening 56 and core element opening 46 so that earphone 22 is positioned adjacent the front surface of core element 34, such as against front portion 48 of covering 36. Muff body 32 is rotated so that headband element 12 projects laterally through gap 76, and cover plate 60 is then pressed onto muff body 32 so that mating strip 70 and 72 firmly, yet releasably secure muff assembly together therefore trapping headband element 12 and earphone 22.

Figure 4:
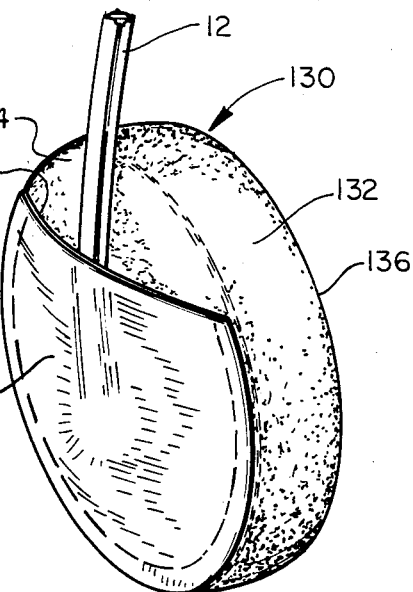
FIG. 4 is a perspective view of an earmuff according to the present invention shown with an alternate attachment structure for securing it to a headset.

An alternate form of securing an earmuff assembly to the assembly is shown in FIG. 4. Here, earmuff assembly 130 includes a muff body 132 formed the same as muff body 32, discussed above. In FIG. 4, however, an elastic panel 134 is sewn around the perimeter of rear surface 154 of thermal covering 136 of muff body 132. Elastic panel 134 accordingly provides a pocket that covers the earphone opening in muff body 132 so that the upper lip 140 of panel 134 may be stretched to allow insertion of an earphone connected to headband member 12 and may then be released to elastically hold muff assembly 130 onto the earphone. The above descriptions show two forms of securing the muff assembly to the headset, namely the cover member 60 and the elastic panel 134. Other known forms of securing means, such as clips that receive the headband or earphone, straps, snaps, and the like are completely within the scope of this invention but are too numerous to describe.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present invention without departing from the inventive concepts contained herein.

I claim:
1. An earmuff releaseably secureable to a headset adapted to be worn on a person's head wherein said headset has an earphone and a headband operative to bias the earphone against the ear, comprising:
   a core element having a soft front surface, a back surface and an opening formed therein through said back surface toward said front surface, said opening sized to telescopically receive said earphone through an entryway of said opening whereby said earphone is surrounded by said core element;
   a thermal protective covering extending across the front surface of said core element, said covering and said core element defining a muff body into which the earphone may be placed; and
   securing means for releaseably securing said muff body to said headset after the earphone is positioned in the muff body whereby the earphone is biased to a location adjacent the ear with the muff body protecting the ear, said securing means including a back cover element extending completely across said entryway to cover said earphone whereby said earphone is enclosed removeably within said core element between said thermal protective covering and said back cover element.

2. An earmuff according to claim 1 wherein said thermal covering overlaps onto the back surface of said core body to form a cover opening coextensive with said entryway.

3. An earmuff according to claim 1 including an annular stiffening plate in said core element operative to strengthen the core element against lateral deflection.

4. An earmuff according to claim 1 wherein said core element is shaped as a torus so that said opening extends completely through the core element, said core element sized to have a thickness so that the headband rests against the back surface and so that the earphone is positioned directly adjacent said covering.

5. An earmuff according to claim 4 wherein said core element is formed by a front annular member and a rear annular member secured together, said front annular member being formed of a soft material.

6. An earmuff according to claim 5 wherein said front annular member is formed of foam rubber.

7. An earmuff according to claim 6 wherein said rear annular member is formed of a soft material and wherein said stiffening plate is located between said front and back annular member and is operative to secure the front and rear annular members together.

8. An earmuff according to claim 1 wherein said back cover element is defined by an inner disc of stiff material and a back covering extending around said inner disc, said back covering formed of the same material as said protective covering.

9. An earmuff according to claim 8 wherein said securing means includes mateable hook and loop fasteners on said cover element and said muff body.

10. An earmuff assembly according to claim 1 wherein said securing means includes an elastic panel extending across a back portion of said muff body and said entryway to elastically retain said earphone therein.

11. An earmuff assembly releaseably secureable to a headset to be worn on a person's head, said headset including an earphone adapted to be positioned adjacent an ear and a headband extending over the head for supporting the earphone, the earmuff assembly adapted to thermally protect the ear without substantially interfering with use of the headset and comprising:

a muff body adapted to receive the earphone and including an annular core element constructed of a soft material and having an axial opening therethrough, said muff body further including a first thermal covering surrounding the core element in a close-fitted manner and having a cover opening on a rear face of said muff body coextensive with a first end of said axial opening, said first covering extending along a front face of said muff body across a second end of said axial opening whereby said earphone may be inserted into a mated position within said axial opening, said core element sized to have a thickness such that the headband rests against the rear face of the muff body with the earphone adjacent the first covering at the front face of the muff body whenin the mated position;

a cover member having a mounting face adapted to be positioned against the rear face of the muff body while said earphone is in the mated position to enclose the cover opening whereby the earphone is retained in the mated position; and cooperative mounting means on said muff body and said cover member for releaseably securing them together.

12. An earmuff assembly according to claim 11 wherein said cover member includes a disc-shaped plate surrounded by a second covering, said plate having a diameter approximately the same as said core member.

13. An earmuff assembly according to claim 12 wherein said mounting means is defined by mateable hook and loop fasteners on said rear face and said mounting face.

14. An earmuff assembly according to claim 13 wherein said mounting means is defined by a C-shaped strip of filiform hooks attached to the rear face of the muff body around the cover opening, said C-shaped strip having ends separated by a narrow gap, said mounting means further defined by an annular strip of loop elements attached to the mounting face, said C-shaped strip and said annular strip having a common diameter and mateable with one another whereby the earphone is retained by said muff assembly with the headband projecting out of the assembly through said gap.

15. An earmuff assembly according to claim 11 wherein said core element is formed by a pair of annular pads of foam rubber attached on opposite sides of an annular disc of relatively stiff plastic material.

* * * * *